(12) United States Patent
Duda

(10) Patent No.: US 7,824,632 B1
(45) Date of Patent: Nov. 2, 2010

(54) DUMPSTER DISINFECTING AND DEODORIZING PROJECTILE

(76) Inventor: Robert Duda, HC-1 Box 403 Brian Dr., Saylorsburg, PA (US) 18353

( * ) Notice: Subject to any disclaimer, the term of this patent is extended or adjusted under 35 U.S.C. 154(b) by 59 days.

(21) Appl. No.: 12/215,972

(22) Filed: Jul. 1, 2008

(51) Int. Cl.
*A61L 2/16* (2006.01)
(52) U.S. Cl. .................... 422/292; 222/608; 222/613; 222/637
(58) Field of Classification Search .......... 422/292; 222/608, 613, 637
See application file for complete search history.

(56) References Cited

U.S. PATENT DOCUMENTS 3,528,662 A * 9/1970 Lloyd et al. ............. 473/577

2004/0140320 A1 * 7/2004 Stravitz .................... 222/52

* cited by examiner

*Primary Examiner*—Sean E Conley

(57) ABSTRACT

A dumpster disinfecting and deodorizing projectile may include a mobile external body, a disinfecting agent contained inside the external body, and a deodorizing agent contained inside the external body. The device may further include a mechanism for automatically releasing the disinfecting and deodorizing agents from the external body after the outer surface is separated to the disengaged particulates and thereby effectively eradicating bacteria and odor over an extended period of time in the existing dumpster. Such an automatic disinfecting agent and deodorizing agent releasing mechanism preferably includes a permeable absorbent pad contiguously lining an inner surface of the external body, and a hollow nucleus that has a cavity formed therein.

12 Claims, 6 Drawing Sheets

DUMPSTER DISINFECTING AND DEODORIZING PROJECTILE

CROSS REFERENCE TO RELATED APPLICATIONS

Not Applicable.

STATEMENT REGARDING FEDERALLY SPONSORED RESEARCH OR DEVELOPMENT

Not Applicable.

REFERENCE TO A MICROFICHE APPENDIX

Not Applicable.

BACKGROUND OF THE INVENTION

1. Technical Field

This invention relates to apparatuses that discharge disinfecting and deodorizing agents and, more particularly, to a dumpster disinfecting and deodorizing projectile for destroying germs and bacteria in an existing dumpster as well as deodorizing ambient air within the existing dumpster.

2. Prior Art

It is well known that organic substances such as residue of foods and fruit juice will be resolved and ferment when it is placed at a position too long. During fermenting, a great amount of bad odor will be released, and it is so bad to suffer such odor that people normally walk fast to pass a heap of garbage with their noses covered in order to avoid smelling the bad odor. In a closed space, such a released bad odor can be much more disgusting. This occurs when organic substance ferments, and in addition to bad odor, heat will be released. Since air flow is retarded in the closed space, temperature therein will be higher than that outside of it, and the higher temperature therein will accelerate fermentation, thereby accelerating the production of bad odors.

Generation of bad odor in such a closed space generally can be the worst in a garbage storing tank and a resources recovery case. This is mainly because they are designed to be sealed in order to prevent bad odor from emitting and to prevent rain from flowing in. Only a throw-in gate is provided for each of them, so that when a user is to throw waste into it, a cover must be lifted up. When the cover is opened, fermentation and rising of temperature therein will render air pressure therein to be slightly higher than that outside of the space, so that at the instant when the cover is opened, air with bad odor in the space will largely emit and rush to the user opening the cover. This is terribly hard to suffer and is very disgusting.

U.S. Pat. No. 4,890,791 to Hoffman discloses a device for use in eliminating malodorous smells from a confined area. The device includes a housing defined by a side-wall and walls closing opposite axial ends thereof. A reservoir is defined within the housing within an annular, interior wall. An annular space is defined, thereby, between the interior wall and the side-wall of the housing. A porous insert formed of fibrous material is received within the annular space. An annular ring of wicking material encircles the insert, and a plurality of angularly-spaced, radially-extending spoke-like wicks extends from the reservoir to the ring wicking material. Liquid neutralizing agent in the reservoir is conducted from the reservoir, through the spoke-like wicks to the ring wicking material, and, in turn, to the porous insert. Unfortunately, this prior art example does not provide a projectile device for one-time use.

U.S. Pat. No. 4,327,056 to Gaiser discloses a deodorant dispensing package having two rates of discharge of deodorant. The package is provided with air circulation ports for a low, continuous release of deodorant and a manual pump for a high, forced rate of deodorant discharge for sudden odors. The package is formed of two telescoping housing members with an internal wall portion that divides the housing into inner and outer compartments. The housing contains a deodorant reservoir and the inner and outer compartments are each provided with vent ports communicating externally of the housing. The inner and outer compartments also communicate through an interior port in the internal wall and a deodorant discharge surface is located in the inner compartment between the inner port and the inner compartment external vent port. Air circulation through the vent ports is sufficient to provide the low rate of air freshener activity. Unfortunately, this prior art example is not designed specifically for eliminating bacteria as well as odor from a garbage receptacle.

Accordingly, the present invention is disclosed in order to overcome the above noted shortcomings. The present invention is convenient and easy to use, lightweight yet durable in design, and designed for destroying germs and bacteria in an existing dumpster as well as deodorizing ambient air within the existing dumpster. The device is simple to use, inexpensive, and designed for efficient use.

BRIEF SUMMARY OF THE INVENTION

In view of the foregoing background, it is therefore an object of the present invention to provide an apparatus for destroying germs and bacteria in an existing dumpster as well as deodorizing ambient air within the existing dumpster. These and other objects, features, and advantages of the invention are provided by a dumpster disinfecting and deodorizing projectile.

A dumpster disinfecting and deodorizing projectile may include a mobile external body that preferably has a cavity formed therein. Such an external body may further have an outer surface provided with lines of weakness formed therein. Such an outer surface is preferably separated into a plurality of disengaged particulates defined by the lines of weakness upon impact.

The device may further include a disinfecting agent contained inside the external body and a deodorizing agent contained inside the external body. Such disinfecting and deodorizing agents may be homogenously mixed together and are non-toxic. The device may further include a mechanism for automatically releasing the disinfecting and deodorizing agents from the external body after the outer surface is separated to the disengaged particulates and thereby effectively eradicating bacteria and odor over an extended period of time in the existing dumpster. Such an automatic disinfecting agent and deodorizing agent releasing mechanism preferably includes a permeable absorbent pad contiguously lining an inner surface of the external body, and a hollow nucleus that has a cavity formed therein. Such a nucleus may be dynamically disposed inside the cavity of the external body and may further be freely movable therein such that the nucleus bounces off the permeable absorbent pad. The nucleus may further include an outer membrane provided with a plurality of permeable egress regions formed therein. Each of the external body and the nucleus preferably has hollow spherical shapes respectively.

The mechanism may further include an agitator dynamically disposed inside the cavity of the nucleus and may be freely movable therein. Such an agitator is preferably randomly displaced within the cavity of the nucleus upon shaking the external body such that the disinfecting and deodorizing agents are dispersed outwardly from the permeable egress outlets and thereafter automatically impregnated into the permeable absorbent pad before the outer surface of the external body is shattered into the particulates respectively. The agitator preferably has a solid spherical shape.

The particulates of the outer surface may be automatically disengaged from the permeable absorbent pad upon impact such that the permeable absorbent pad is exposed to ambient air and thereby outwardly releases the disinfecting and deodorizing agents therefrom. The permeable absorbent pad preferably maintains a single and unitary annular shape after impact such that the nucleus is prohibited from escaping through the permeable absorbent pad.

A preferable method for destroying germs and bacteria in an existing dumpster as well as deodorizing ambient air within the existing dumpster may include the steps of: providing a mobile external body that has a cavity formed therein, the external body further having an outer surface provided with lines of weakness formed therein; providing a non-toxic disinfecting agent contained inside the external body; providing a non-toxic deodorizing agent contained inside the external body; impacting the external body against a dumpster; separating the outer surface into a plurality of disengaged particulates defined by the lines of weakness and thereby automatically releasing the disinfecting and deodorizing agents from the external body; and effectively eradicating bacteria and odor over an extended period of time in the existing dumpster.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

It is noted the purpose of the foregoing abstract is to enable the U.S. Patent and Trademark Office and the public generally, especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

BRIEF DESCRIPTION OF THE SEVERAL VIEWS OF THE DRAWING

The novel features believed to be characteristic of this invention are set forth with particularity in the appended claims. The invention itself, however, both as to its organization and method of operation, together with further objects and advantages thereof, may best be understood by reference to the following description taken in connection with the accompanying drawings in which:

DETAILED DESCRIPTION OF THE INVENTION

Figure 1:
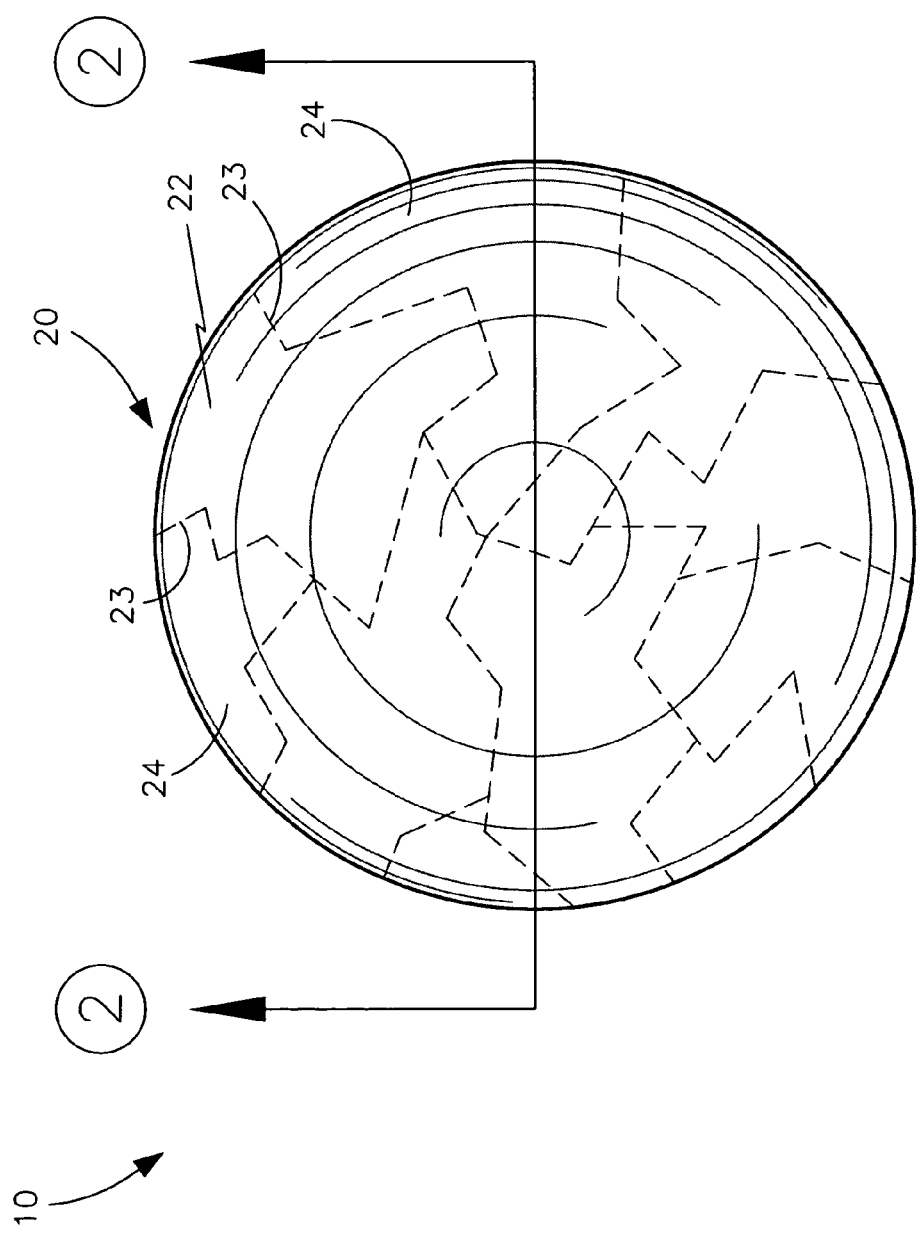
FIG. 1 is a top plan view of the dumpster disinfecting and deodorizing projectile, in accordance with the present invention.

The present invention will now be described more fully hereinafter with reference to the accompanying drawings, in which a preferred embodiment of the invention is shown. This invention may, however, be embodied in many different forms and should not be construed as limited to the embodiment set forth herein. Rather, this embodiment is provided so that this application will be thorough and complete, and will fully convey the true scope of the invention to those skilled in the art. Like numbers refer to like elements throughout the figures.

The device of this invention is referred to generally in FIGS. 1-6 by the reference numeral 10 and is intended to provide a dumpster disinfecting and deodorizing projectile. It should be understood that the apparatus 10 may be used to deodorize and disinfect many different types of odorous enclosures and should not be limited in use with only those types of enclosures mentioned here.

Referring initially to FIGS. 1 through 4, a dumpster disinfecting and deodorizing projectile 10 may include a mobile external body 20 that preferably has a cavity 21 formed therein. Such an external body 20 may further have an outer surface 22 provided with lines of weakness 23 formed therein. Such an outer surface 22 is preferably separated into a plurality of disengaged particulates 24 defined by the lines of weakness 23 upon impact. The combination of the external body 20 and the lines of weakness 23 provides the unpredictable and unexpected result of ensuring that the body 20, upon being impacted, easily breaks into particulates 24, thereby exposing the disinfecting and deodorizing components of the device 10.

Referring to FIGS. 2, 4, 5 and 6, the device 10 may further include a disinfecting agent 25A contained inside the external body 20 and a deodorizing agent 25B contained inside the external body 20. Such disinfecting and deodorizing agents 25A, 25B may be homogenously mixed together and are non-toxic. One skilled in the art understands that various well known disinfecting and deodorizing agents are commercially available, which are in either liquid or powder form. Such agents 25A, 25B are preferably injected into a nucleus 29 (described hereinbelow) by way of conventional and well known methods in the industry.

Likewise, the nucleus 29 may be seated inside a half-shell or complete mold of the external body 20 before the body 20 is formed via well known and conventional injection molding procedures, for example. It is understood that one skilled in the art knows how to make and use the present invention without performing undue experimentation by following well known industry standards for encapsulating one spherical object into another spherical object, for example.

The device 10 may further include a mechanism 26 for automatically releasing the disinfecting and deodorizing agents 25A, 25B from the external body 20 after the outer surface 22 is separated to the disengaged particulates 24 and thereby effectively eradicating bacteria and odor over an extended period of time in the existing dumpster 11.

Such an automatic disinfecting agent and deodorizing agent releasing mechanism 26 preferably includes a permeable absorbent pad 27 contiguously lining an inner surface 28 of the external body 20, and a hollow nucleus 29 that has a cavity 30 formed therein. Such a nucleus 29 may be dynamically disposed inside the cavity 21 of the external body 20 and may further be freely movable therein such that the nucleus 29 bounces off the permeable absorbent pad 27.

The nucleus 29 may further include an outer membrane 31 provided with a plurality of permeable egress regions 32 formed therein. Each of the external body 20 and the nucleus 29 preferably has hollow spherical shapes respectively. The combination of the disinfecting and deodorizing agents 25A, 25B provide the unexpected benefit of both hiding and eliminating bad odors simultaneously, thereby limiting a user's exposure to unpleasant smells. Again, one skilled in the art knows how to make and use the present invention without performing undue experimentation by following well known industry standards for forming the absorbent pad 27 around the nucleus 29 and thereafter forming the outer body 20 about the absorbent pad 27, for example.

Figure 2:
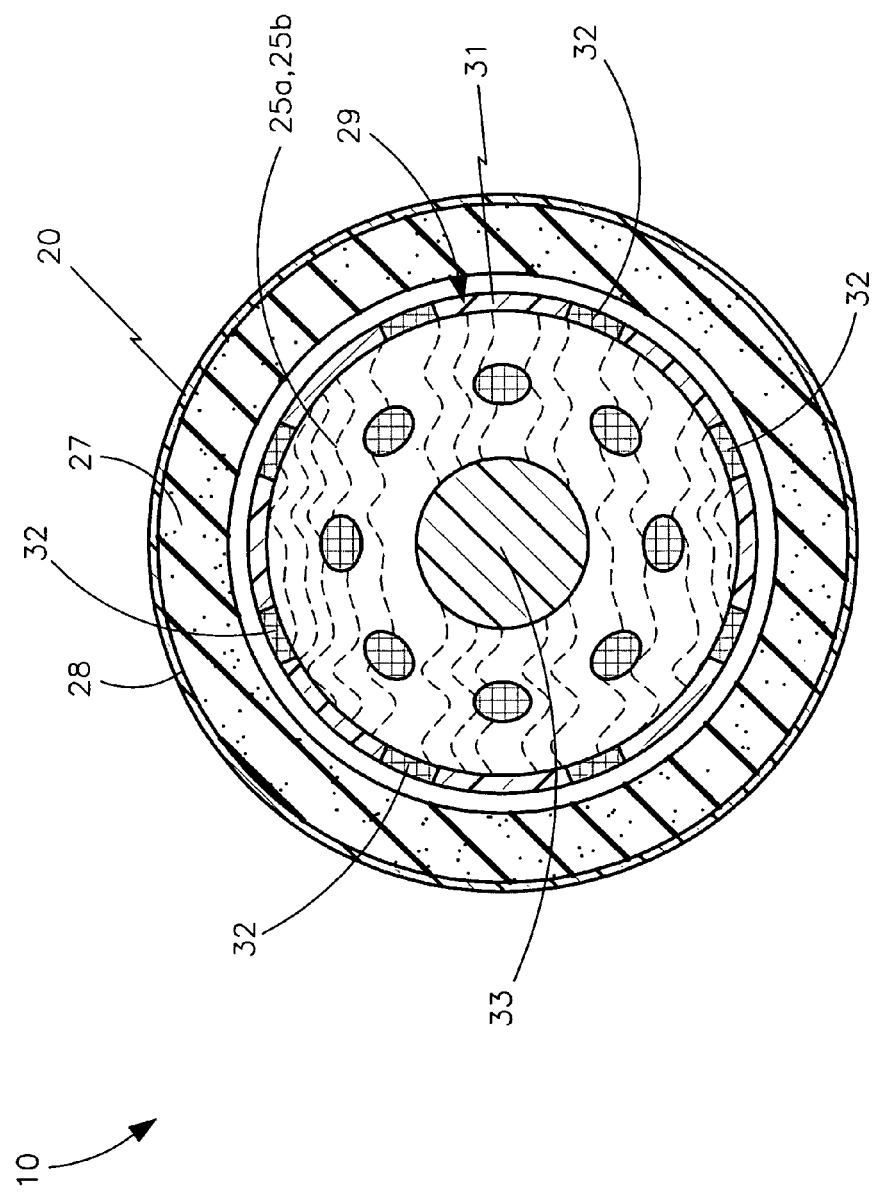
FIG. 2 is a cross sectional view of the present invention, taken along line 2-2, as seen in FIG. 1.
Figure 3:
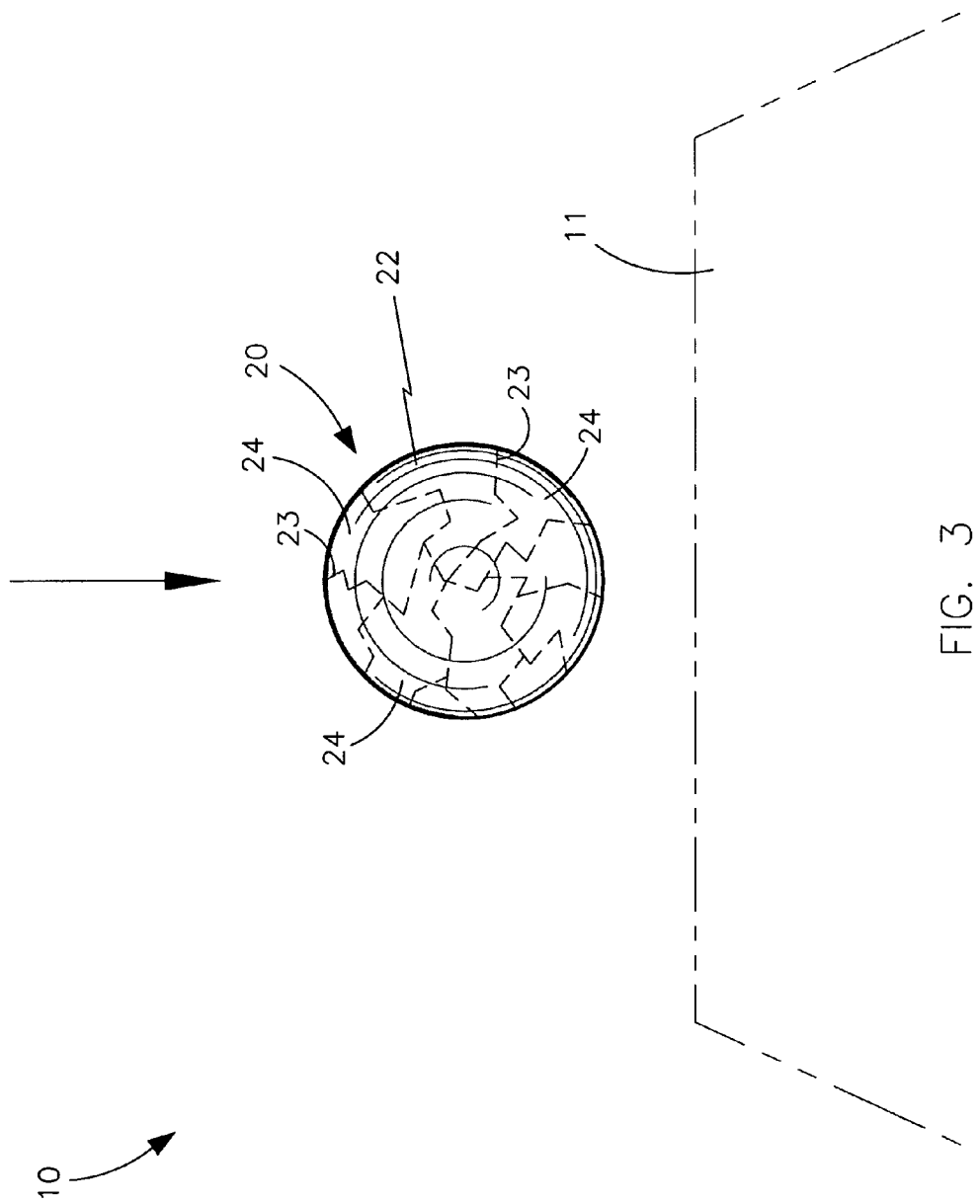
FIG. 3 is a perspective view of the dumpster disinfecting and deodorizing projectile entering an existing garbage receptacle.
Figure 4:
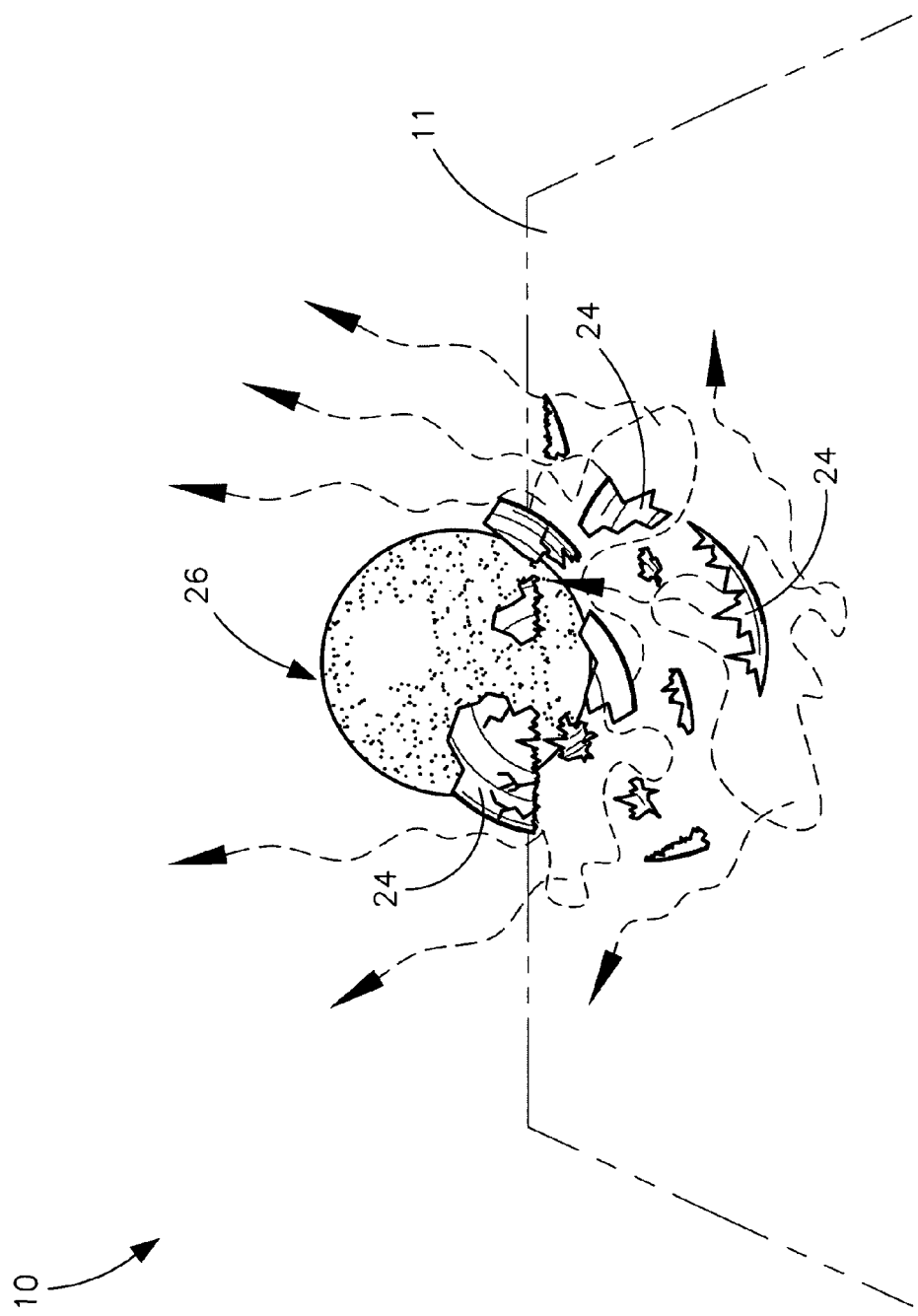
FIG. 4 is a perspective view of the projectile as seen in FIG. 3, showing the exposure of the permeable absorbent layer to ambient air.
Figure 5:
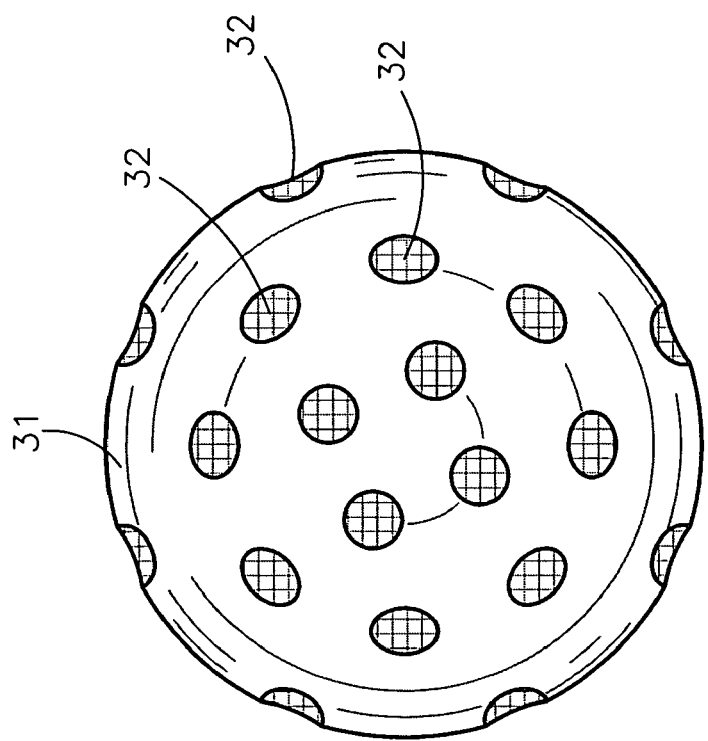
FIG. 5 is an enlarged view of the nucleus, in accordance with the present invention.
Figure 6:
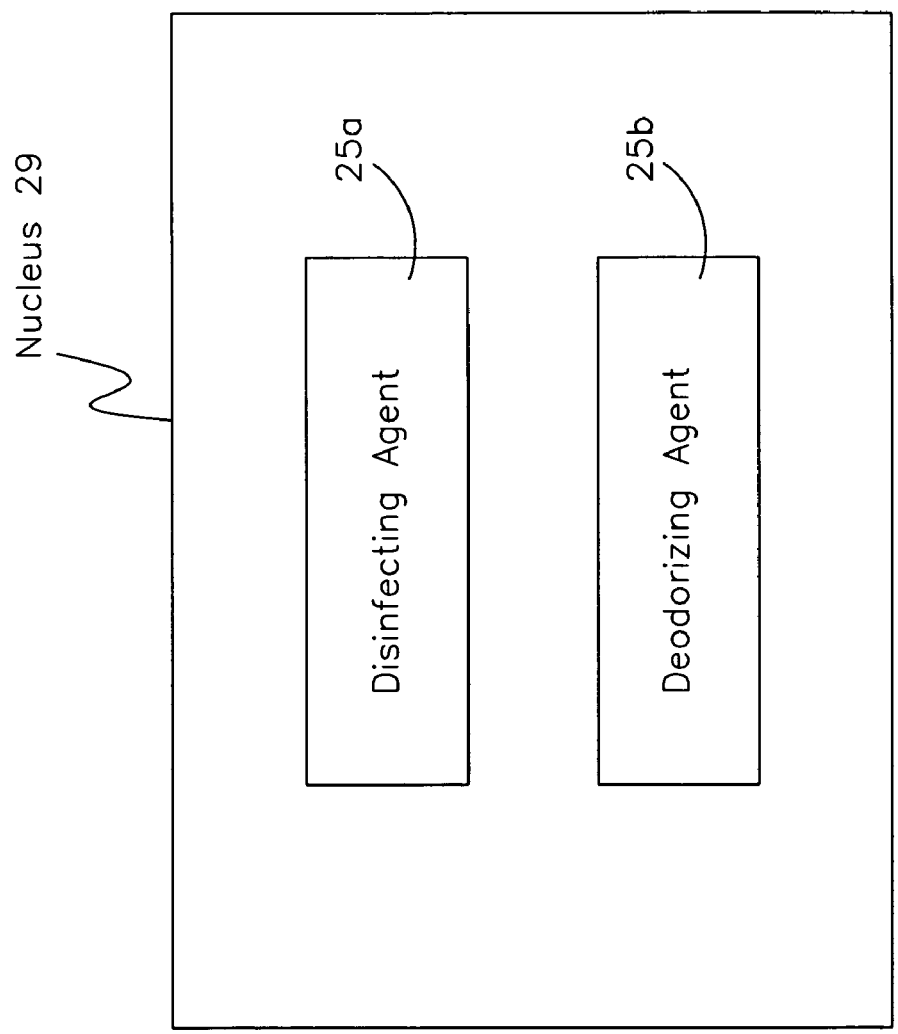
FIG. 6 is a block diagram showing the nucleus and its homogenous mixture of disinfecting and deodorizing agents housed therein, in accordance with the present invention.

Referring to FIG. 2, the mechanism 26 may further include an agitator 33 dynamically disposed inside the cavity 30 of the nucleus 29 and may be freely movable therein. Such an agitator 33 is preferably randomly displaced within the cavity 30 of the nucleus 29 upon shaking the external body 20 which is essential such that the disinfecting and deodorizing agents 25A, 25B are dispersed outwardly from the permeable egress outlets 32 and thereafter automatically impregnated into the permeable absorbent pad 27 before the outer surface 22 of the external body 20 is shattered into the particulates respectively. The agitator 33 preferably has a solid spherical shape. The agitator 33 provides the unexpected benefit of pushing the disinfecting and deodorizing agents 25A, 25B towards the egress outlets 32, thereby ensuring that when the external body 20 is shattered, the agents 25A, 25B are released into the ambient air and/or discharged along a bottom surface of the garbage receptacle.

The particulates 24 of the outer surface 22 may be automatically disengaged from the permeable absorbent pad 27 upon impact which is crucial such that the permeable absorbent pad 27 is exposed to ambient air and thereby outwardly releases the disinfecting and deodorizing agents 25A, 25B therefrom. The permeable absorbent pad 27 preferably maintains a single and unitary annular shape after impact which is important such that the nucleus 29 is prohibited from escaping through the permeable absorbent pad 27.

In use, a preferable method for destroying germs and bacteria in an existing dumpster 11 as well as deodorizing ambient air within the existing dumpster may include the steps of: providing a mobile external body 20 that has a cavity 21 formed therein, the external body 20 further having an outer surface 22 provided with lines of weakness 23 formed therein; providing a non-toxic disinfecting agent 25A contained inside the external body 20; providing a non-toxic deodorizing agent 25B contained inside the external body 20; impacting the external body 20 against a dumpster 11; separating the outer surface 22 into a plurality of disengaged particulates 24 defined by the lines of weakness 23 and thereby automatically releasing the disinfecting and deodorizing agents 25A, 25B from the external body 20; and effectively eradicating bacteria and odor over an extended period of time in the existing dumpster 11.

In one embodiment, the present invention 10 may include a sphere-shaped external body 20 that is specially designed to burst and activate when impacted on the inner surface of an existing garbage receptacle 11, for example. Such a device 10 may measure 2 inches in diameter, for example. Of course, the device 10 may be produced in a variety of alternate shapes and sizes, as is obvious to a person of ordinary skill in the art. The external body 20 preferably has a durable yet breakable plastic or cardboard outer shell. Inside the body 20 may be disinfecting and deodorizing agents 25A, 25B preferably comprised of nontoxic, environmentally safe glycol microparticles that, upon release, linger in the air, attaching to airborne bacteria and odor molecules. Of course, the disinfectant and deodorizer 25A, 25B could be produced in a variety of fragrances, such as refreshing citrus, floral, or pine to name a few options, as is obvious to a person of ordinary skill in the art.

In use, a preferable method for sanitizing garbage receptacles and the like is simple and straightforward to operate. First, the user should remove the device 10 from its packaging. After opening the lid of the dumpster 11 or household receptacle, the user may forcefully pitch the device 10 against the interior wall of the container. When the projectile 10 strikes, the external body 20 will break and thereby release the inner disinfectant and deodorant 25A, 25B. The user then closes the lid to effectively contain the vapor, advantageously allowing it to eradicate the odors and bacteria. Pungent smells are thus neutralized, which is crucial for allowing a pleasant scent to penetrate.

The present invention, as claimed, provides the unexpected and unpredictable benefit of providing a disposable projectile 10 that is convenient and easy to use, is versatile in its applications, and offers user a disinfectant/deodorizer in a most convenient and easy to use external body 20. The creatively incorporated, breakable external body 20 allows for easy application of the wonderful formula that kills the toughest germs and odors. The present invention effectively freshens any garbage dumpster as well as household trash cans of various sizes. The device 10 is especially beneficial to restaurants and other dining establishments, as it eliminates the dreadful odors that can detract from an appetizing atmosphere as well as raise objections during health inspections.

While the invention has been described with respect to a certain specific embodiment, it will be appreciated that many modifications and changes may be made by those skilled in the art without departing from the spirit of the invention. It is intended, therefore, by the appended claims to cover all such modifications and changes as fall within the true spirit and scope of the invention.

In particular, with respect to the above description, it is to be realized that the optimum dimensional relationships for the parts of the present invention may include variations in size, materials, shape, form, function and manner of operation. The assembly and use of the present invention are deemed readily apparent and obvious to one skilled in the art.

What is claimed as new and what is desired to secure by Letters Patent of the United States is:

1. A dumpster disinfecting and deodorizing projectile for destroying germs and bacteria in an existing dumpster as well as deodorizing ambient air within the existing dumpster, said dumpster disinfecting and deodorizing projectile comprising:

an external body having a cavity formed therein, said external body further having an outer surface provided with lines of weakness formed therein, said outer surface being separated into a plurality of disengaged particulates defined by said lines of weakness upon impact;

a disinfecting agent contained inside said external body;

a deodorizing agent contained inside said external body; and means for automatically releasing said disinfecting and deodorizing agents from said external body after said outer surface is separated to said disengaged particulates and thereby effectively eradicating bacteria and odor over an extended period of time in the existing dumpster;

wherein said automatic disinfecting agent and deodorizing agent releasing means comprises:

a permeable absorbent pad contiguously lining an inner surface of said external body;

a hollow nucleus having a cavity formed therein, said nucleus being dynamically disposed inside said cavity of said external body and being freely movable therein such that said nucleus bounces off said permeable absorbent pad, said nucleus including an outer membrane provided with a plurality of permeable egress regions formed therein; and an agitator dynamically disposed inside said cavity of nucleus and being freely movable therein;

wherein said agitator is randomly displaced within said cavity of said nucleus upon shaking said external body such that said disinfecting and deodorizing agents are dispersed outwardly from said permeable egress outlets and thereafter automatically impregnated into said permeable absorbent pad before said outer surface of said external body is shattered into said particulates respectively.

2. The dumpster disinfecting and deodorizing projectile of claim 1, wherein said particulates of said outer surface are automatically disengaged from said permeable absorbent pad upon impact such that said permeable absorbent pad is exposed to ambient air and thereby outwardly releases said disinfecting and deodorizing agents therefrom.

3. The dumpster disinfecting and deodorizing projectile of claim 1, wherein said permeable absorbent pad maintains a single and unitary annular shape after impact such that said nucleus is prohibited from escaping through said permeable absorbent pad.

4. The dumpster disinfecting and deodorizing projectile of claim 1, wherein said disinfecting and deodorizing agents are homogenously mixed together.

5. The dumpster disinfecting and deodorizing projectile of claim 1, wherein said agitator has a solid spherical shape.

6. The dumpster disinfecting and deodorizing projectile of claim 1, wherein each of said external body and said nucleus have hollow spherical shapes respectively.

7. A dumpster disinfecting and deodorizing projectile for destroying germs and bacteria in an existing dumpster as well as deodorizing ambient air within the existing dumpster, said dumpster disinfecting and deodorizing projectile comprising:

a mobile external body having a cavity formed therein, said external body further having an outer surface provided with lines of weakness formed therein, said outer surface being separated into a plurality of disengaged particulates defined by said lines of weakness upon impact;

a disinfecting agent contained inside said external body;

a deodorizing agent contained inside said external body; and means for automatically releasing said disinfecting and deodorizing agents from said external body after said outer surface is separated to said disengaged particulates and thereby effectively eradicating bacteria and odor over an extended period of time in the existing dumpster;

wherein said disinfecting and deodorizing agents are non-toxic;

wherein said automatic disinfecting agent and deodorizing agent releasing means comprises:

a permeable absorbent pad contiguously lining an inner surface of said external body;

a hollow nucleus having a cavity formed therein, said nucleus being dynamically disposed inside said cavity of said external body and being freely movable therein such that said nucleus bounces off said permeable absorbent pad, said nucleus including an outer membrane provided with a plurality of permeable egress regions formed therein; and an agitator dynamically disposed inside said cavity of nucleus and being freely movable therein;

wherein said agitator is randomly displaced within said cavity of said nucleus upon shaking said external body such that said disinfecting and deodorizing agents are dispersed outwardly from said permeable egress outlets and thereafter automatically impregnated into said permeable absorbent pad before said outer surface of said external body is shattered into said particulates respectively.

8. The dumpster disinfecting and deodorizing projectile of claim 7, wherein said particulates of said outer surface are automatically disengaged from said permeable absorbent pad upon impact such that said permeable absorbent pad is exposed to ambient air and thereby outwardly releases said disinfecting and deodorizing agents therefrom.

9. The dumpster disinfecting and deodorizing projectile of claim 7, wherein said permeable absorbent pad maintains a single and unitary annular shape after impact such that said nucleus is prohibited from escaping through said permeable absorbent pad.

10. The dumpster disinfecting and deodorizing projectile of claim 7, wherein said disinfecting and deodorizing agents are homogenously mixed together.

11. The dumpster disinfecting and deodorizing projectile of claim 7, wherein said agitator has a solid spherical shape.

12. The dumpster disinfecting and deodorizing projectile of claim 7, wherein each of said external body and said nucleus have hollow spherical shapes respectively.

* * * * *